(12) United States Patent
Henkelmann et al.

(10) Patent No.: US 7,053,244 B2
(45) Date of Patent: May 30, 2006

(54) METHOD FOR THE CONTINUOUS PRODUCTION OF TETRA-SUBSTITUTED UREAS

(75) Inventors: Jochem Henkelmann, Mannheim (DE); Theodor Weber, Ludwigshafen (DE); Thorsten Rohde, Mannheim (DE); Ralph Busch, Worms (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/520,402

(22) PCT Filed: Jul. 3, 2003

(86) PCT No.: PCT/EP03/07083

§ 371 (c)(1),
(2), (4) Date: Jan. 6, 2005

(87) PCT Pub. No.: WO2004/007436

PCT Pub. Date: Jan. 22, 2004

(65) Prior Publication Data

US 2005/0261524 A1    Nov. 24, 2005

(30) Foreign Application Priority Data

Jul. 10, 2002    (DE) ............................. 102 310 858

(51) Int. Cl.
 *C07C 273/18*    (2006.01)
(52) U.S. Cl. .............................. 564/55; 564/57; 564/61
(58) Field of Classification Search ................. 564/55, 564/57, 61
 See application file for complete search history.

(56) References Cited

U.S. PATENT DOCUMENTS 3,681,457 A * 8/1972 Babad ........................... 564/61
3,904,602 A * 9/1975 Somlo .......................... 564/61
5,132,423 A    7/1992 Brunelle et al.

FOREIGN PATENT DOCUMENTS

| EP | 0248 220 | 12/1987 |
| JP | 59 031 752 | 2/1984 |
| WO | WO 94/22939 | 10/1994 |

OTHER PUBLICATIONS

International Search Report, Oct. 2003, PCT/EP20003/007083.
Ullmann's Encyclopedia of Industrial Chemistry, 6$^{th}$ Edition, 2000 Electronic Release, Urea-Urea Derivatives-Meessen, et al., pp. 1-10.
W.A. Skinner et al., J. Pharm. Sci 68, vol. No. 3, pp. 391-392, Mar. 1979; Topical Mosquito Repellents XIII; N-Substituted Ureas and Cyclic Ureas.

* cited by examiner

*Primary Examiner*—Peter O'Sullivan
(74) *Attorney, Agent, or Firm*—Connolly Bove Lodge & Hutz LLP

(57) ABSTRACT

The invention relates to a process for the preparation of tetrasubstituted ureas by reaction of the corresponding amines with phosgene in the presence of an aqueous inorganic base at a temperature in the range from 0 to 150° C., which comprises:

feeding the corresponding amine, the phosgene and the aqueous inorganic base on average continuously to the reaction apparatus, forming a two-phase system in the reaction apparatus through the choice of the tetrasubstituted ureas to be prepared, through the mixing ratios of the substances and substance mixtures to be fed in, through the temperature during the reaction and, where appropriate, through the feed of an organic solvent which is not completely miscible with water, and discharging the reaction mixture on average continuously from the reaction apparatus.

20 Claims, No Drawings

METHOD FOR THE CONTINUOUS PRODUCTION OF TETRA-SUBSTITUTED UREAS

RELATED APPLICATIONS

This application is a National Stage application of PCT/EP03/07083 filed on Jul. 3, 2003, which claims benefit to German application 102 31 085.8 filed Jul. 10, 2002.

The present invention relates to a process for the preparation of tetrasubstituted ureas by reaction of the corresponding amines with phosgene in the presence of an aqueous inorganic base at a temperature in the range from 0 to 150° C.

N-substituted ureas are widely used in the preparation of crop-protection products, pharmaceuticals and dyes. They are furthermore employed as plasticizers and stabilizers in plastics, as lubricants and as catalysts, for example as phosgenation catalysts. N-substituted ureas are furthermore employed as polar aprotic solvents, where they are particularly important as substitute for highly toxic phosphoric acid amides, such as hexamethylphosphoric acid triamide (HMPA) and hexamethylphosphorous acid triamide (HMPT). N-alkylureas and N-polyalkyleneureas are in addition used as additives in the preparation of amino plastics.

In industry, N-substituted ureas are predominantly prepared by transamidation of urea with amines, by alkylation of urea with alcohols, by reaction of amines with cyanates and by phosgenation of amines (see Ullmann's Encyclopedia of Industrial Chemistry, 6$^{th}$ Edition, 2000 electronic release, Chapter "UREA—Urea derivatives").

JP 9031-752-A and U.S. Pat. No. 3,681,457 describe the discontinuous preparation of tetramethylurea by introduction of phosgene into a flask containing dimethylamine and aqueous sodium hydroxide solution or potassium hydroxide solution, and subsequently extracting the aqueous phase with a water-insoluble solvent, such as n-hexane, chloroform or ethylene dichloride, and isolating the tetramethylurea from the organic phase.

U.S. Pat. No. 5,132,423 discloses the discontinuous preparation of tetraethylurea by introducing phosgene into a flask containing diethylamine, ethylene chloride and aqueous sodium hydroxide solution, subsequently separating the two phases after the reaction is complete, and isolating the tetraethylurea from the organic phase.

EP-A 0 248 220 teaches the discontinuous preparation of cyclic ureas by introducing phosgene into a flask containing N,N'-dialkyldiamine and aqueous sodium hydroxide solution, and extracting the resultant mixture with 1,2-dichloroethane.

W. A. Skinner et al. in *J. Pharm. Sci.* 68, 1979, pages 391 to 392, teach the discontinuous preparation of tetrabutylurea by dropwise addition of dibutylamine into a flask containing benzene, phosgene and potassium carbonate, subsequently stirring the mixture at room temperature for three hours, adding further dibutylamine, refluxing the mixture for three hours, subsequently filtering off the solid phase containing potassium carbonate and potassium chloride, and working up the filtrate by distillation. According to the preparation procedure, a total of 31.25 ml of dibutylamine (0.184 mol) were employed. With a total volume of the liquid phase of about 0.28 l (benzene, phosgene, potassium carbonate and dibutylamine) and a total time for the reaction of 6.5 hours (dropwise addition of dibutylamine for 0.5 hour, stirring at room temperature for 3 hours and refluxing for 3 hours), a space-time yield of only at most 14 g/l·h arises, even for an assumed yield for tetrabutylurea of 100%.

The above-mentioned processes are very labor-intensive and expensive, especially in the case of the preparation of relatively large amounts of tetrasubstituted ureas, since a plurality of batches may have to be carried out one after the other, depending on the reactor size. Thus, the reaction apparatus should be filled with the corresponding amine and aqueous hydroxide solution at the beginning and brought to the reaction temperature. Only on subsequent introduction of phosgene does the chemical reaction also start. When the reaction is complete, the reaction apparatus should be emptied and prepared for the next batch. The reaction apparatus is thus only utilized for a certain proportion of the time for the actual chemical reaction, with the consequence that a low space-time yield also results.

Furthermore, the extraction of tetramethylurea with an organic solvent which is to be carried out after the reaction is disadvantageous in the two above-mentioned processes for the preparation of tetramethylurea since this means a further, separate process step.

It is an object of the present invention to find a process for the preparation of tetrasubstituted ureas which does not have the above-mentioned disadvantages and which enables the preparation of relatively large amounts with a high space-time yield.

We have found that this object is achieved by a process for the preparation of tetrasubstituted ureas by reaction of the corresponding amines with phosgene in the presence of an aqueous inorganic base at a temperature in the range from 0 to 150° C., which comprises feeding the corresponding amine, the phosgene and the aqueous inorganic base on average continuously to the reaction apparatus, forming a two-phase system in the reaction apparatus through the choice of the tetrasubstituted ureas to be prepared, through the mixing ratios of the substances and substance mixtures to be fed in, through the temperature during the reaction and, where appropriate, through the feed of an organic solvent which is not completely miscible with water, and discharging the reaction mixture on average continuously from the reaction apparatus.

The process according to the invention is thus a continuous process and has a two-phase system in the reaction apparatus. This comprises an aqueous, liquid phase and an organic, liquid phase.

In the process according to the invention, the corresponding amine, the phosgene and the aqueous inorganic base are fed on average continuously to the reaction apparatus, and the reaction mixture is discharged on average continuously from the reaction apparatus. The term "on average continuous feed or discharge" is also taken to mean periodic or aperiodic fluctuations in the amount fed in or discharged as for pulse-like feed or discharge. The feed or discharge of a constant or virtually constant amount is preferred.

In order also to enable continuous and constant operation of the process according to the invention over an extended period, it is advantageous to operate the reaction apparatus with a constant or virtually constant fill volume (fill level) and to control the amount to be discharged via the desired fill volume (fill level).

The formation of a two-phase system in the reaction apparatus is achieved in the process according to the invention by various measures:

a) through the choice of the tetrasubstituted ureas to be prepared

Depending on the nature of the substituents, the tetrasubstituted ureas to be prepared are completely soluble, soluble to a certain extent or only very sparingly soluble or virtually insoluble in water. In the case of tetrasubstituted ureas which are not completely soluble in water, an organic phase may therefore already form, depending on the relative mixing ratios and the temperature.)

b) Through the mixing ratios of the substances and substance mixtures to be fed in The mixing ratios of the substances and substance mixtures to be fed in have an effect on the mixing ratios of the inorganic and organic substances present in the reaction apparatus and thus, in combination with the solubility properties of the tetrasubstituted ureas, also on the formation of a two-phase system. Thus, it is, for example, advantageous in the preparation of tetrasubstituted ureas which are soluble to a certain extent in water to employ a slightly smaller amount of aqueous phase. In order nevertheless to prepare the requisite amount of inorganic base in this case, a more highly concentrated aqueous inorganic base may have to be fed in.

c) Through the temperature during the reaction

Since the solubility properties of the tetrasubstituted ureas are also dependent on the temperature, the prevailing temperature also has an influence on the formation of a two-phase system. However, it should be emphasized that when selecting the reaction temperature, other parameters, such as the reaction rate, the pressure prevailing in the reaction apparatus or the formation of undesired by-products, are also influenced and should advantageously be balanced against one another.

d) Where appropriate through the feed of an inorganic solvent which is not completely miscible with water into the reaction apparatus Furthermore, an organic solvent which is not completely miscible with water can also be fed in during the process according to the invention. This also facilitates the formation of a two-phase system where the above-mentioned measures a) to c) are not sufficient. Thus, for example, the feed of an organic solvent which is not completely miscible with water is also capable of forming an organic phase in the preparation of tetrasubstituted ureas which are completely miscible with water. Owing to the solubility properties of the tetrasubstituted urea, the latter is generally then present to a significant proportion in the organic phase. Furthermore, the addition of an organic solvent which is not completely miscible with water is capable of keeping tetrasubstituted ureas which would be in the form of a solid under the reaction conditions in solution.

Any organic solvents which are not completely miscible with water that are to be employed should advantageously be chemically inert under the reaction conditions set, i.e. do not react chemically with the compounds employed, have a good solubility property for the tetrasubstituted urea to be dissolved, and should be removable from the tetrasubstituted urea in a simple manner, for example by distillation. Suitable solvents which may be mentioned are chlorinated hydrocarbons, for example dichloromethane, trichloromethane and dichloroethane; saturated aliphatic or cyclic hydrocarbons, for example hexane, heptane, isooctane and cyclohexane; aromatic hydrocarbons, for example benzene, toluene and xylene; and halogenated aromatic hydrocarbons, for example chlorobenzene and dichlorobenzene.

For each system, it is possible to determine by means of simple experiments whether a two-phase system is present or not under the desired conditions. If a two-phase system is not present, a two-phase system can be set specifically through the above-mentioned measures b), c) and/or d) in the case of a specified tetrasubstituted urea.

Through the above-mentioned measures, the formation of a two-phase system is ensured. In principle, it is more advantageous for the process according to the invention the smaller the amount of tetrasubstituted urea dissolved in the aqueous phase. The proportion of tetrasubstituted urea present in the aqueous phase in the process according to the invention is preferably $\leq 5\%$ and particularly preferably $\leq 1\%$ of the total amount of tetrasubstituted urea present.

The tetrasubstituted ureas which can be prepared by the process according to the invention have the general formula (I)

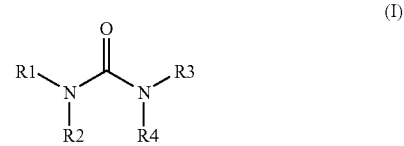

where the radicals $R^1$ to $R^4$ are carbon-containing organic radicals, which may also, if desired, be bonded to one another.

The term "carbon-containing organic radical" is taken to mean an unsubstituted or substituted, aliphatic, aromatic or araliphatic radical. This may contain one or more heteroatoms, for example oxygen, nitrogen, sulfur or phosphorus, for example —O—, —S—, —NR—, —CO—, —N=, —PR— and/or —PR$_2$, and/or be substituted by one or more functional groups which contain, for example, oxygen, nitrogen, sulfur and/or halogen, for example by fluorine, chlorine, bromine, iodine and/or a cyano group (where the radical R is likewise a carbon-containing organic radical). The carbon-containing organic radical can be a monovalent or a divalent, trivalent or tetravalent radical.

If two or more of the radicals $R^1$ and $R^4$ are bonded to one another, these are preferably the radicals $R^2$ with $R^4$ or $R^1$ with $R^2$ and/or $R^3$ with $R^4$.

As monovalent radicals, the radicals $R^1$ to $R^4$ are preferably, independently of one another, an unbranched or branched, acyclic or cyclic, unsubstituted or substituted alkyl radical having from 1 to 30 aliphatic carbon atoms, in which one or more of the CH$_2$ groups may also be replaced by heteroatoms, such as —O— or —S—, or by groups containing a heteroatom, such as —CO— or —NR—, and in which one or more of the hydrogen atoms may be replaced by substituents, for example aryl groups or functional groups; or an unsubstituted or substituted aromatic radical having from 3 to 30 carbon atoms and one ring or two or three fused rings, in which one or more ring atoms may be substituted by heteroatoms, for example nitrogen, and in which one or more of the hydrogen atoms may be replaced by substituents, for example alkyl or aryl groups or functional groups.

As divalent radicals, the radicals $R^1$ with $R^2$ and/or $R^3$ with $R^4$ are preferably an unbranched or branched, acyclic or cyclic, unsubstituted or substituted $C_4$- to $C_{20}$-alkylene radical ("divalent alkyl radical") having from 4 to 10 atoms in the alkylene chain, in which CH$_2$ groups may also be replaced by hetero groups, for example —CO—, —O— or —NR—, and in which one or more of the hydrogen atoms may be replaced by substituents, for example alkyl or aryl groups.

As divalent radicals, the radicals $R^2$ with $R^4$ are preferably an unbranched or branched, acyclic or cyclic, unsubstituted or substituted $C_2$- to $C_{20}$-alkylene radical ("divalent alkyl radical") having from 2 to 10 atoms in the alkylene chain, in which $CH_2$ groups may also be replaced by hetero groups, for example —CO—, —O— or —NR—, and in which one or more of the hydrogen atoms may be replaced by substituents, for example alkyl or aryl groups.

Particular preference is given to the preparation of tetrasubstituted ureas (I)

(i) whose radicals $R^1$ to $R^4$ are an unbranched or branched $C_1$- to $C_{20}$-alkyl radical, for example methyl, ethyl, 1-propyl, 2-propyl(sec-propyl), 1-butyl, 2-butyl(sec-butyl), 2-methyl-1-propyl(iso-butyl), 2-methyl-2-propyl(tert-butyl), 1-pentyl, 2-pentyl, 3-pentyl, 2-methyl-2-butyl(tert-amyl), 1-hexyl, 2-hexyl, 3-hexyl, 2-methyl-2-pentyl or 3-methyl-3-pentyl;

an unbranched or branched $C_5$- to $C_{20}$-cycloalkyl radical, for example cyclopentyl, cyclohexyl or cyclooctyl; or a $C_6$- to $C_{20}$-aryl or $C_3$- to $C_{20}$-heteroaryl radical which is unsubstituted or substituted by one or more $C_1$- to $C_4$-alkyl radicals, for example phenyl, 2-methylphenyl (o-tolyl), 3-methylphenyl(m-tolyl), 4-methylphenyl(p-tolyl), 2,6-dimethylphenyl, 2,4-dimethylphenyl, 2,4,6-trimethylphenyl, 2-methoxyphenyl, 3-methoxyphenyl, 4-methoxyphenyl, 2-pyridyl, 3-pyridyl, 4-pyridyl, 3-pyridazinyl, 4-pyridazinyl, 5-pyridazinyl, 2-pyrimidinyl, 4-pyrimidinyl, 5-pyrimidinyl, 2-pyrazinyl, 2-(1,3,5-triazin)yl, 1-naphthyl, 2-naphthyl, 2-quinolyl, 8-quinolyl, 1-isoquinolyl or 8-isoquinolyl;

(ii) whose radicals $R^1$ with $R^2$ and $R^3$ with $R^4$ are bonded and are an unbranched or branched, unsubstituted or substituted $C_4$- to $C_{10}$-alkylene radical ("divalent alkyl radical") having from 4 to 10 atoms in the alkylene chain, in which $CH_2$ groups may also be replaced by hetero groups, for example —CO—, —O— or —NR—, and in which one or more of the hydrogen atoms may be replaced by substituents, for example alkyl or aryl groups, for example butylene, pentylene, hexylene, —$CH_2CH_2$—O—$CH_2CH_2$— or —$CH_2CH_2$—NR—$CH_2CH_2$—; or (iii) whose radicals $R^1$ and $R^4$ are as mentioned under (i) and the radicals $R^2$ with $R^3$ are bonded and are an unbranched or branched, unsubstituted or substituted $C_2$- to $C_{10}$-alkylene radical ("divalent alkyl radical") having from 2 to 10 atoms in the alkylene chain, in which $CH_2$ groups may also be replaced by hetero groups, for example —CO—, —O— or —NR—, and in which one or more of the hydrogen atoms may be replaced by substituents, for example alkyl or aryl groups, for example ethylene, propylene, butylene, pentylene, hexylene, —$CH_2CH_2$—O—$CH_2CH_2$— or —$CH_2CH_2$—NR—$CH_2CH_2$—.

In the process according to the invention, the tetrasubstituted ureas prepared are very particularly preferably the symmetrically tetrasubstituted ureas N,N,N',N'-tetramethylurea, N,N,N',N'-tetraethylurea, N,N,N',N'-tetrapropylurea, N,N,N',N'-tetrabutylurea, N,N,N',N'-tetrapentylurea, N,N,N',N'-tetrahexylurea, N,N,N',N'-tetra(cyclopropyl)urea, N,N,N',N'-tetra(cyclohexyl)urea, N,N,N',N'-tetraphenylurea, bis(butylene)urea, bis(pentylene)urea, N,N'-dimethylethyleneurea, N,N'-dimethylpropyleneurea, N,N'-dimethyl (2-(methylaza)propylene)urea and N,N'-dimethyl(3-(methylaza)pentylene)urea.

In the process according to the invention, the tetrasubstituted ureas prepared are in particular N,N,N',N'-tetrabutylurea, N,N'-dimethylethyleneurea and N,N'-dimethylpropyleneurea.

The corresponding amines to be employed are the amines $HNR^1R^2$ and $HNR^3R^4$, where, in accordance with the above description, the radicals $R^1$ to $R^4$ may also, if desired, be bonded to one another. Thus, the corresponding amine to be employed in the preparation of N,N,N',N'-tetrabutylurea is dibutylamine and the corresponding amine to be employed in the preparation of N,N'-dimethylpropyleneurea is N,N'-dimethylpropane-1,3-diamine.

The feed of the amine can take place in various ways. It can in principle be fed in as a liquid and/or gas. Furthermore, the amine to be fed in can be added, for example, in pure form or diluted with an inert gas or an organic solvent which is not completely miscible with water.

The feed of the phosgene can likewise be carried out in various ways, for example in liquid and/or gaseous form or in pure form or diluted with an inert gas or an organic solvent which is not completely miscible with water. Preference is given to the addition of liquid or gaseous phosgene without dilution.

The aqueous inorganic base is an aqueous solution of an inorganic base. Examples which may be mentioned are ammonia water, sodium hydroxide solution and potassium hydroxide solution.

The inorganic base to be fed in serves for binding the hydrogen chloride formerly formed in the reaction of the corresponding amines with phosgene. In order to prevent or reduce to a minimum a competing reaction with the corresponding amine, which functions as starting material for the preparation of the substituted ureas, it is particularly advantageous to employ an aqueous inorganic base which has a lower $pK_b$ value, measured at 25° C. in aqueous solution, than the corresponding amine.

The aqueous inorganic base employed in the process according to the invention is very particularly preferably sodium hydroxide solution and/or potassium hydroxide solution.

The molar ratio between the phosgene to be fed in and the corresponding amine to be fed in is generally from 0.3 to 0.8 and preferably from 0.4 to 0.6 in the case of amines having one NH group and from 0.6 to 1.6 and preferably from 0.8 to 1.2 in the case of amines having two NH groups (for the preparation of cyclic ureas).

The molar ratio between the inorganic base to be fed in and the corresponding amine to be fed in is generally from 0.5 to 2 and preferably from 0.7 to 1.5 in the case of amines having one NH group and from 1.0 to 4 and preferably from 1.4 to 3 in the case of amines having two NH groups (for the preparation of cyclic ureas).

The reaction is preferably carried out at a pH of ≧9, particularly preferably of ≧10 and very particularly preferably of from 10 to 12. It has proven particularly advantageous here to regulate the feed of aqueous inorganic base via the pH desired in the reaction mixture.

As already mentioned above, the presence of an organic solvent which is not completely miscible with water is necessary in the preparation of tetrasubstituted ureas which are completely miscible with water or very readily soluble in water in order to ensure the formation of a two-phase system in the reaction apparatus. The solvent fed in should then generally be removed again during the subsequent work-up, which means additional work. Tetrasubstituted ureas having lower solubility in water can therefore particularly advantageously be prepared by the process according to the invention since the amount of organic solvent which is not completely miscible with water that is to be fed in can be significantly smaller or may even be omitted entirely. In the process according to the invention, preference is therefore given to the preparation of tetrasubstituted ureas which have a solubility in water of $\leq 10$ g/l of water and particularly preferably of $\leq 2$ g/l of water, measured at 25° C. and atmospheric pressure.

As likewise already mentioned above, tetrasubstituted ureas whose melting point is above the reaction temperature generally likewise require dissolution in an organic solvent which is not completely miscible with water. Tetrasubstituted ureas having a melting point below the reaction temperature can therefore particularly advantageously be prepared by the process according to the invention since the amount of organic solvent which is not completely miscible with water that is to be fed in can be significantly smaller or can even be omitted entirely. In the process according to the invention, preference is therefore given to the preparation of tetrasubstituted ureas which have a melting point of $\leq 150°$ C. and particularly preferably of $\leq 100°$ C.

The process according to the invention is preferably carried out at a temperature of from 10 to 100° C. and particularly preferably of from 50 to 85° C. When the process is carried out, the pressure is generally from 0.05 to 1.0 MPa abs., preferably from 0.08 to 0.2 MPa abs. and very particularly preferably from 0.08 to 0.12 MPa abs.

Reaction apparatuses which can be employed in the process according to the invention are in principle the apparatuses described in the expert literature for gas-liquid reactions, or, in the case of the use of liquid phosgene, the known apparatuses for liquid-liquid reactions. Examples of suitable reaction apparatuses which may be mentioned are stirred-tank reactors, flow tubes (preferably with internals), bubble columns and loop reactors.

The reaction is preferably carried out in a stirred-tank reactor. In order to ensure efficient input, the phosgene is preferably introduced through the stirrer and/or through nozzles.

In a particularly preferred variant, the reaction is carried out in a cascade of at least two stirred-tank reactors. The first stirred-tank reactor here functions as so-called main reactor, to which the starting materials, i.e. the corresponding amine, the phosgene, the aqueous inorganic base and, where appropriate, the organic solvent which is not completely miscible with water, are fed on average continuously with vigorous mixing and in which partial conversion to the tetrasubstituted urea takes place. Preferably, from 10 to 95% of the tetrasubstituted urea are formed in the main reactor. The two-phase reaction mixture from the main reactor, which comprises the inorganic base, the chloride formed, the unreacted amine, the disubstituted carbamic acid chloride as intermediate, the tetrasubstituted urea and any unreacted phosgene and solvent added, is then fed on average continuously to the second stirred-tank reactor. This functions as so-called post-reactor, in which the remainder of the reaction, in particular the reaction between the disubstituted carbamic acid chloride and the still-free amine takes place. In general, no further starting materials are fed to the post-reactor. If necessary, however, it is possible, for example in order to achieve the overall stoichiometry, to feed in further starting material, for example phosgene or the corresponding amine. Intensive mixing is also ensured in the post-reactor.

In general, one post-reactor is sufficient, i.e. the particularly preferred stirred-tank reactor cascade thus comprises two stirred-tank reactors. The volume ratio between the main reactor and the post-reactor is advantageously from 0.1 to 4 and preferably from 0.5 to 2.

On use of a stirred-tank reactor, the on average continuous discharge of the reaction mixture takes place via an appropriately positioned outflow or withdrawal device. This can be, for example, an aperture in the wall of the stirred-tank reactor or a dip tube.

In a particularly preferred variant of the process according to the invention, part of the reaction mixture is discharged from the region close to the liquid surface and a further part is discharged from the region close to the bottom of the stirred-tank reactor. In general, the two discharged streams are combined and fed to further work-up or, in the case of a reactor cascade, into the subsequent reactor. The particularly preferred embodiment mentioned increases the proportion of organic phase in the stirred-tank reactor and reduces the proportion of aqueous phase. The reason for this is the knowledge that, in spite of intense mixing, the distribution of organic and aqueous phase in the stirred-tank reactor is not precisely even, and a somewhat increased proportion of aqueous phase is present in the region close to the bottom. The said increase in the proportion of the organic phase results in a further increase in the space-time yield.

The continuous process can be started up in various ways. However, it must be ensured that the heat liberated by the exothermic reaction can be correspondingly dissipated. For this reason, the feed of the respective third reaction component, in particular, should be carried out particularly carefully. After initiation of the reaction, all three reaction components can then usually be fed in continuously. In a variant, the corresponding amine is initially introduced, phosgene is passed in, and further amine and the aqueous inorganic base are subsequently fed in continuously. When the desired fill level has been reached, the reaction mixture is discharged on average continuously from the reaction apparatus. In another variant, the initially introduced amine can also be diluted with the organic solvent which is not completely miscible with water or with reaction mixture from a prior production campaign, and the remainder of the process carried out as described above. This enables particularly gentle start-up.

Irrespective of the type of reaction apparatus employed or the number of reaction apparatuses, the process according to the invention firstly gives a two-phase reaction mixture. The aqueous phase here predominantly comprises any excess of inorganic base, the chloride formed and possibly, depending on solubility, fractions of organic compounds. The organic phase predominantly comprises the tetrasubstituted urea and any unreacted amine, unreacted disubstituted carbamic acid chloride and intermediate and, depending on solubility, fractions of the aqueous phase. During work-up, the two-phase reaction mixture is usually separated into the two phases. This can be carried out, for example, in a so-called settler as phase-separation vessel. In general, it is advantageous subsequently to wash the isolated organic phase with water in order to remove further water-soluble substances. The tetrasubstituted urea can then be isolated from the organic phase. The isolation is preferably carried out by distillation. In the first distillation step, the low-boiling components, for example residual water and unreacted amine, are separated off at the top of the column. In a second distillation step, the tetrasubstituted urea is then obtained at the top of the column.

In a particularly preferred embodiment, the corresponding amine and the aqueous inorganic base are initially introduced into the first stirred-tank reactor, which functions as main reactor, and warmed to the desired reaction temperature, and phosgene gas is introduced with stirring to the desired pH. For safety reasons, it is generally advantageous only to fill the stirred-tank reactor to a proportion of from about 20 to 50%. The continuous feed of the amine and of the aqueous inorganic base is generally then begun, with further phosgene correspondingly being passed in continuously. When the desired fill level has been reached, reaction mixture is passed continuously from the main reactor into the second stirred-tank reactor, which functions as post-reactor. This can be operated with or without temperature control. When the post-reactor has also been filled to the desired fill level with stirring, the reaction mixture is also discharged continuously therefrom. The reaction mixture is passed into a so-called settler for phase separation, and the organic phase is washed with water. The organic phase is subsequently worked up by conventional methods, with distillative work-up being preferred.

The process according to the invention enables the continuous preparation of tetrasubstituted ureas while avoiding the time-consuming, labor-intensive and energy-consuming working steps necessary in the discontinuous processes which are usual in the industry, with higher selectivity, higher space-time yield and thus higher productivity in a simple manner. Thus, the process according to the invention enables a space-time yield of several hundred g/l·h in the preparation of N,N,N',N'-tetrabutylurea.

The particularly preferred process according to the invention for the preparation of tetrasubstituted ureas which have a solubility in water of ≦10 g/l of water, measured at 25° C. and atmospheric pressure, and a melting point below the reaction temperature enables the reaction to be carried out without addition of a solvent. Owing to the higher concentration of starting materials which is possible, a particularly high space-time yield and particularly simple work-up are thereby possible.

EXAMPLES

Example 1

40 g of 23.8% by weight aqueous sodium hydroxide solution and 24 g of dibutylamine were introduced into a 0.8 l stirred-tank reactor with overflow and warmed to 75° C. In order to start up the reactor, phosgene gas was then passed in at this temperature until the pH of the reaction mixture had dropped to a value in the range from 10 to 11. Further 23.8% by weight aqueous sodium hydroxide solution and dibutylamine were subsequently fed in at this temperature, with the feed rates being set in such a way that a pH of approximately 11 was maintained in the reactor. When the desired fill level in the reactor had been reached, the continuous process was begun, and 194 g (1.5 mol) of dibutylamine, 97 g of phosgene and 518 g of 23.8% by weight sodium hydroxide solution were fed in over the course of 6 hours at a reaction temperature of 75° C., and the reaction mixture was discharged continuously via the overflow. The two-phase discharge was separated via a phase separator into the aqueous phase and the organic phase. In total, 231 g of organic phase were obtained. This comprised 88.2 GC area-% of N,N,N',N'-tetrabutylurea, 9.3 GC area-% of unreacted dibutylamine and 0.8 GC area-% of N,N-dibutylcarbamic acid chloride. The yield of N,N,N',N'-tetrabutylurea was 88%, based on the dibutylamine employed. The space-time yield achieved during continuous operation was thus [(1.5 mol/2)·0.88·284 g/mol]/0.8 1·6 h=39.1 g/l·h.

Example 2

The experiment plant comprised a stirred-tank reactor cascade with a 0.3 l stirred-tank reactor as main reactor, a 0.5 l stirred-tank reactor as post-reactor and a downstream 0.2 l settler. In order to start up the experiment plant, the main reactor was filled with crude discharge obtained in accordance with Example 1 comprising organic and aqueous phase, and warmed to 50° C. The continuous process was then begun, and 360 g (2.79 mol) of dibutylamine, 132 g of phosgene and 1015 g of 15% by weight aqueous sodium hydroxide solution were introduced over the course of 5.75 hours at a reaction temperature of 50° C., with the pH in the main reactor being held at a value of approximately 11 via the metering of the sodium hydroxide solution. The post-reactor remained unheated. The reaction mixture was passed continuously from the main reactor via an overflow into the post-reactor and, after the latter had been filled, was pumped via a further overflow into the settler, where the phase separation was carried out. The collected organic phase of the discharge comprised 88.2 GC area-% of N,N,N',N'-tetrabutylurea, 11.3 GC area-% of unreacted dibutylamine and 0.15 GC area-% of N,N-dibutylcarbamic acid chloride.

Example 3

The experiment plant comprised a stirred-tank reactor cascade with a 0.5 l stirred-tank reactor as main reactor, a 0.3 l stirred-tank reactor as post-reactor and a downstream 0.2 l settler. In order to start up the experiment plant, the main reactor was filled with crude discharge obtained in accordance with Example 2 comprising organic and aqueous phase, and warmed to 75° C. The continuous process was then begun, and 763 g (5.91 mol) of dibutylamine, 292 g of phosgene and 1441 g of 15% by weight aqueous sodium hydroxide solution were introduced over the course of 6 hours at a reaction temperature of 75° C., with the pH in the main reactor being held at a value of approximately 11 via the metering of the sodium hydroxide solution. The post-reactor remained unheated. The reaction mixture was passed continuously from the main reactor via an overflow (withdrawal point 5 cm below the fill level) into the post-reactor and, after the latter had been filled, was pumped into the settler, where the phase separation was carried out. A total of 815 g of organic phase was obtained, which comprised 90.7 GC area-% of N,N,N',N'-tetrabutylurea, 8.8 GC area-% of unreacted dibutylamine and 0.01 GC area-% of N,N-dibutylcarbamic acid chloride. The yield of N,N,N',N'-tetrabutylurea was 88%, based on the dibutylamine employed. The space-time yield achieved during continuous operation was thus [(5.91 mol/2)·0.88·284 g/mol]/0.8 1·6 h=154 g/l·h.

Example 4

The experiment plant comprised a stirred-tank reactor cascade with a 0.5 l stirred-tank reactor as main reactor, a 0.5 l stirred-tank reactor as post-reactor and a downstream 0.2 l settler. In order to start up the experiment plant, the main reactor was filled with crude discharge obtained in accordance with Example 2 comprising organic and aqueous phase, and warmed to 85° C. The continuous process was then begun, and 1374 g (10.7 mol) of dibutylamine, 533 g of phosgene and 2931 g of 15% by weight aqueous sodium hydroxide solution were introduced over the course of 7 hours at a reaction temperature of 85° C., with the pH in the main reactor being held at a value of approximately 11 via the metering of the sodium hydroxide solution. The post-reactor remained unheated. The reaction mixture was passed continuously from the main reactor via an overflow (withdrawal point 5 cm below the fill level) into the post-reactor and, after the latter had been filled, was pumped into the settler, where the phase separation was carried out. A total of 1522 g of organic phase was obtained, which comprised 92.5 GC area-% of N,N,N',N'-tetrabutylurea, 7.6 GC area-% of unreacted dibutylamine and 0.02 GC area-% of N,N-dibutylcarbamic acid chloride. The yield of N,N,N',N'-tetrabutylurea was 93%, based on the dibutylamine employed. The space-time yield achieved during continuous operation was thus [(10.7 mol/2)·0.925·284 g/mol]/1.0 l·7 h=201 g/l·h.

enables a further significant increase in the space-time yield by about 25% to 201 g/l·h.

Example 5 shows compared with Example 4 the effect of the size of the main reactor. Due to the reduction in the size of the main reactor from 0.5 l to 0.3 l, the space-time yield dropped significantly to about half and was 95.5 g/l·h in spite of the enlargement of the post-reactor from 0.5 l to 0.6 l.

TABLE 1

Overview of the reaction conditions and results from Examples 1 to 5

| Example | Number of successive stirred-tank reactors | Volume of main reactor [l] | Volume of post-reactor [l] | Total reaction volume [l] | Reaction temperature [° C.] | Space-time yield [g/l · h] |
|---|---|---|---|---|---|---|
| 1 | 1 | 0.8 | — | 0.8 | 75 | 39.1 |
| 3 | 2 | 0.5 | 0.3 | 0.8 | 75 | 154 |
| 4 | 2 | 0.5 | 0.5 | 1.0 | 85 | 201 |
| 5 | 2 | 0.3 | 0.6 | 0.9 | 85 | 95.5 |

Example 5

The experiment plant comprised a stirred-tank reactor cascade with a 0.3 l stirred-tank reactor as main reactor, a 0.6 l stirred-tank reactor as post-reactor and a downstream 0.2 l settler. In order to start up the experiment plant, the main reactor was filled with crude discharge obtained in accordance with Example 2 comprising organic and aqueous phase, and warmed to 85° C. The continuous process was then begun, and 534 g (4.14 mol) of dibutylamine, 250 g of phosgene and 1450 g of 15% by weight aqueous sodium hydroxide solution were introduced over the course of 6.5 hours at a reaction temperature of 85° C., with the pH in the main reactor being held at a value of approximately 11 via the metering of the sodium hydroxide solution. The post-reactor remained unheated. The reaction mixture was passed continuously from the main reactor via an overflow into the post-reactor and, after the latter had been filled, was pumped into the settler, where the phase separation was carried out. A total of 760 g of organic phase was obtained, which comprised 91.4 GC area-% of N,N,N',N'-tetrabutylurea, 8.19 GC area-% of unreacted dibutylamine and 0.06 GC area-% of N,N-dibutylcarbamic acid chloride. The yield of N,N,N',N'-tetrabutylurea was 95%, based on the dibutylamine employed. The space-time yield achieved during continuous operation was thus [(4.14 mol/2)·0.95·284 g/mol]/0.9 l·6.5 h=95.5 g/l·h.

Table 1 gives an overview of the reaction conditions and the results from Examples 1 to 5.

Compared with the discontinuous process for the preparation of N,N,N',N'-tetrabutylurea described in W. A. Skinner et al. in J. Pharm. Sci. 68, 1979, pages 391 to 392, in which a space-time yield of only 14 g/l·h was achieved, the continuous process from Example 1 according to the invention enables an approximately 2.8-times higher yield of 39.1 g/l·h.

A comparison of Example 1 with Example 3 shows that, with the same reaction temperature and same total reaction volume, a cascaded process with a main reactor and a post-reactor results in a significant increase in the space-time yield. In the present case, the cascaded process in Example 3 enabled a space-time yield almost four times higher to be achieved than in the one-step process in Example 1.

Example 4 shows compared with Example 3 that an increase in the reaction temperature from 75° C. to 85° C. and an enlargement of the post-reactor from 0.3 l to 0.5 l

We claim:

1. A process for the preparation of tetrasubstituted ureas comprising:
   reacting, in a reaction apparatus, at least one corresponding amine with phosgene in the presence of an aqueous inorganic base at a temperature in the range of from 0° C. to 150° C., said process further comprising:
   feeding the at least one corresponding amine, the phosgene and the aqueous inorganic base on average continuously to the reaction apparatus,
   forming a two-phase system in the reaction apparatus through the choice of:
   (i) the tetrasubstituted ureas to be prepared;
   (ii) the mixing ratios of the substances and substance mixtures to be fed in;
   (iii) the temperature during the reaction; and, optionally
   (iv) the feed of an organic solvent which is not completely miscible with water; and
   discharging the reaction mixture on average continuously from the reaction apparatus.

2. The process according to claim 1, wherein the tetrasubstituted ureas to be prepared have a solubility in water of ≦10 g/l of water, measured at 25° C. and atmospheric pressure.

3. The process according to claim 1, wherein the tetrasubstituted ureas to be prepared have a melting point of ≦150° C.

4. The process according to claim 1, wherein the aqueous inorganic base has a lower $pK_b$ value, measured at 25° C. in aqueous solution, that the corresponding amine.

5. The process according to claim 1, wherein the aqueous inorganic base comprises at least one base selected from the group consisting of aqueous sodium hydroxide solution and aqueous potassium hydroxide solution.

6. The process according to claim 1, wherein the reaction is carried out at a pressure in the range from 0.05 MPa to 1.0 MPa.

7. The process according to claim 1, wherein the reaction is carried out in a stirred-tank reactor.

8. The process according to claim 1, wherein the reaction is carried out in a cascade of at least two stirred-tank reactors.

9. The process according to claim 7 or 8, wherein part of the reaction mixture is discharged from a region close to the liquid surface of the reaction mixture and a further part of the reaction mixture is discharged from a region close to the bottom of the stirred-tank reactor or reactors.

10. The process according to claim 1, wherein the process results in the preparation of at least one tetrasubstituted urea selected from the group consisting of N,N,N',N'-tetrabutylurea, N,N'-dimethylethyleneurea, and N,N'-dimethylpropyleneurea.

11. The process according to claim 2, wherein the tetrasubstituted ureas to be prepared have a melting point of $\leq 150°$ C.

12. The process according to claim 2, wherein the aqueous inorganic base has a lower $pK_b$ value, measured at 25° C. in aqueous solution, that the corresponding amine.

13. The process according to claim 3, wherein the aqueous inorganic base has a lower $pK_b$ value, measured at 25° C. in aqueous solution, that the corresponding amine.

14. The process according to claim 11, wherein the aqueous inorganic base has a lower $pK_b$ value, measured at 25° C. in aqueous solution, that the corresponding amine.

15. The process according to claim 2, wherein the aqueous inorganic base comprises at least one base selected from the group consisting of aqueous sodium hydroxide solution and aqueous potassium hydroxide solution.

16. The process according to claim 3, wherein the aqueous inorganic base comprises at least one base selected from the group consisting of aqueous sodium hydroxide solution and aqueous potassium hydroxide solution.

17. The process according to claim 4, wherein the aqueous inorganic base comprises at least one base selected from the group consisting of aqueous sodium hydroxide solution and aqueous potassium hydroxide solution.

18. The process according to claim 2, wherein the reaction is carried out at a pressure in the range from 0.05 MPa to 1.0 MPa.

19. The process according to claim 3, wherein the reaction is carried out at a pressure in the range from 0.05 MPa to 1.0 MPa.

20. The process according to claim 4, wherein the reaction is carried out at a pressure in the range from 0.05 MPa to 1.0 MPa.

* * * * *